United States Patent [19]
Pennig

[11] Patent Number: 5,304,177
[45] Date of Patent: Apr. 19, 1994

[54] AUXILIARY DEVICE FOR OSTEOSYNTHESIS

[76] Inventor: Dietmar Pennig, Hans-Driesch-Strasse 12, 5000 Cologne, Fed. Rep. of Germany

[21] Appl. No.: 77,803

[22] Filed: Jan. 3, 1994

Related U.S. Application Data

[63] Continuation-in-part of Ser. No. 58,502, May 5, 1993, abandoned.

[30] Foreign Application Priority Data

Jun. 26, 1992 [DE] Fed. Rep. of Germany ....... 4220936

[51] Int. Cl.⁵ .............................................. A61B 17/56
[52] U.S. Cl. ........................................ 606/58; 606/59; 403/374; 403/396; 403/90
[58] Field of Search ................ 606/53, 54, 55, 57, 606/58, 59, 105; 403/343, 374, 373, 396, 384, 83, 84, 90, 101, 112, 113

[56] References Cited

U.S. PATENT DOCUMENTS

| | | |
|---|---|---|
| Re. 31,809 | 1/1985 | Danieletto et al. . |
| 2,346,346 | 4/1944 | Anderson . |
| 2,391,693 | 12/1945 | Ettinger .................... 606/57 |
| 4,244,360 | 1/1981 | Dohogne . |
| 4,988,349 | 1/1991 | Pennig .................... 606/58 |

FOREIGN PATENT DOCUMENTS

| | | |
|---|---|---|
| 0011258 | 5/1980 | European Pat. Off. . |
| 0024256 | 2/1988 | European Pat. Off. . |
| 0420813 | 4/1991 | European Pat. Off. . |
| 0490812 | 6/1992 | European Pat. Off. . |
| 0517939 | 12/1992 | European Pat. Off. . |
| 2531332 | 2/1984 | France . |
| 2574653 | 6/1986 | France . |
| 2628627 | 9/1989 | France . |
| 1333327 | 8/1987 | U.S.S.R. ................... 606/54 |
| 2240043 | 7/1991 | United Kingdom . |
| 8805287 | 7/1988 | World Int. Prop. O. . |

*Primary Examiner*—Tamara L. Graysay
*Attorney, Agent, or Firm*—Hopgood, Calimafde, Kalil, Blaustein & Judlowe

[57] ABSTRACT

An external fixator for osteosynthesis features application to the fixation of fractures of small bones such as those of the hand or foot. A small central unit contains two ball joints which are releasably clamped via a single actuation. Bone fasteners, such as bone pins or bone screws are releasably clamped, via a single actuation at each of two clamping units, and each of the clamping units is adjustably clamped to a carrier rod within a wide range of selected positions, which extends to the smallest of offsets from the central double-ball joint unit, by reason of the fact that the ball of each ball joint is the inner end of one of the respective carrier rods.

23 Claims, 2 Drawing Sheets

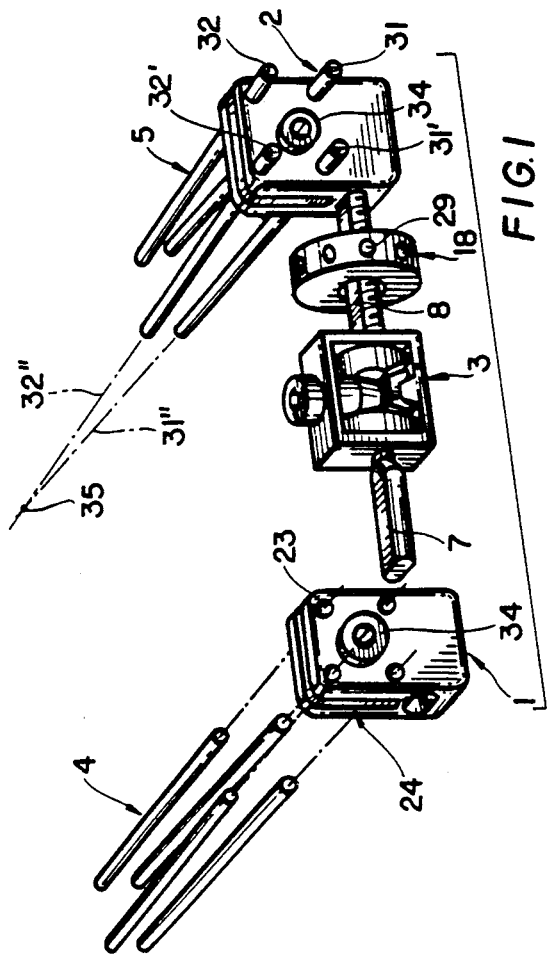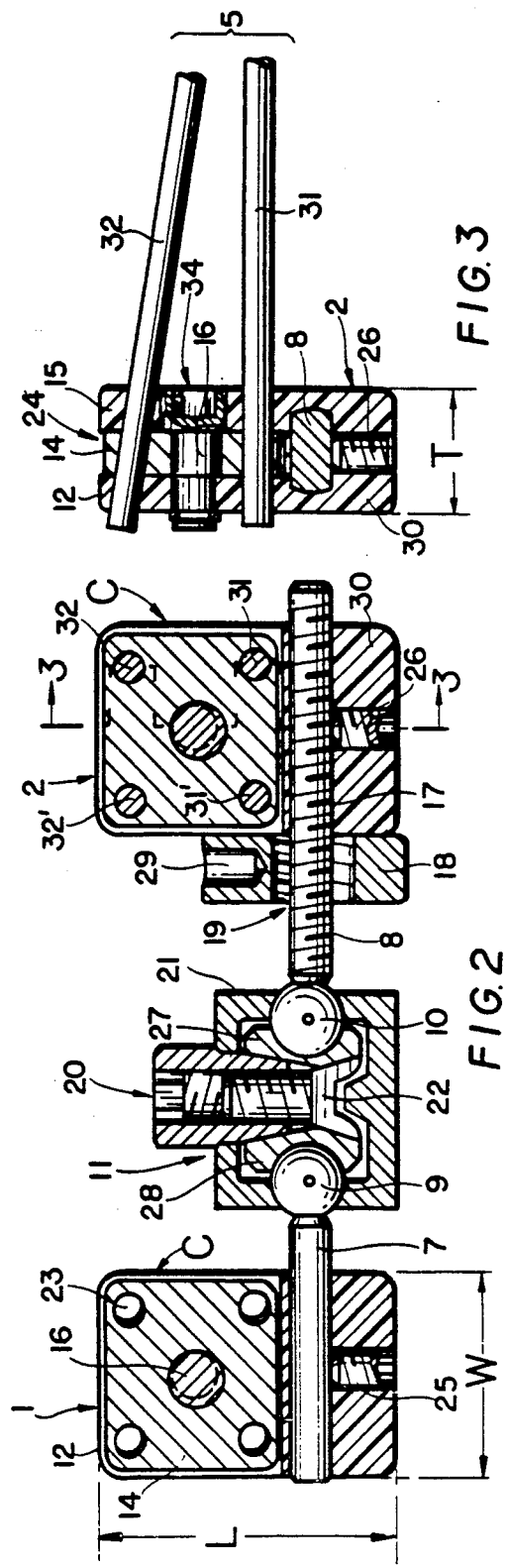

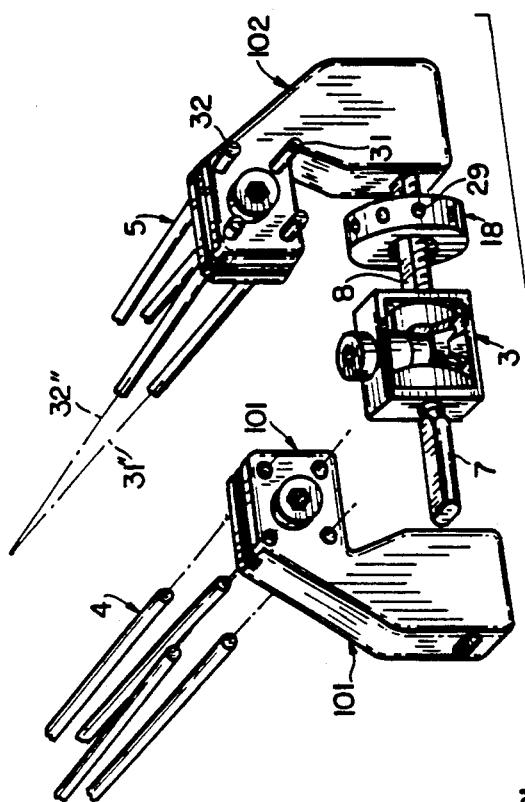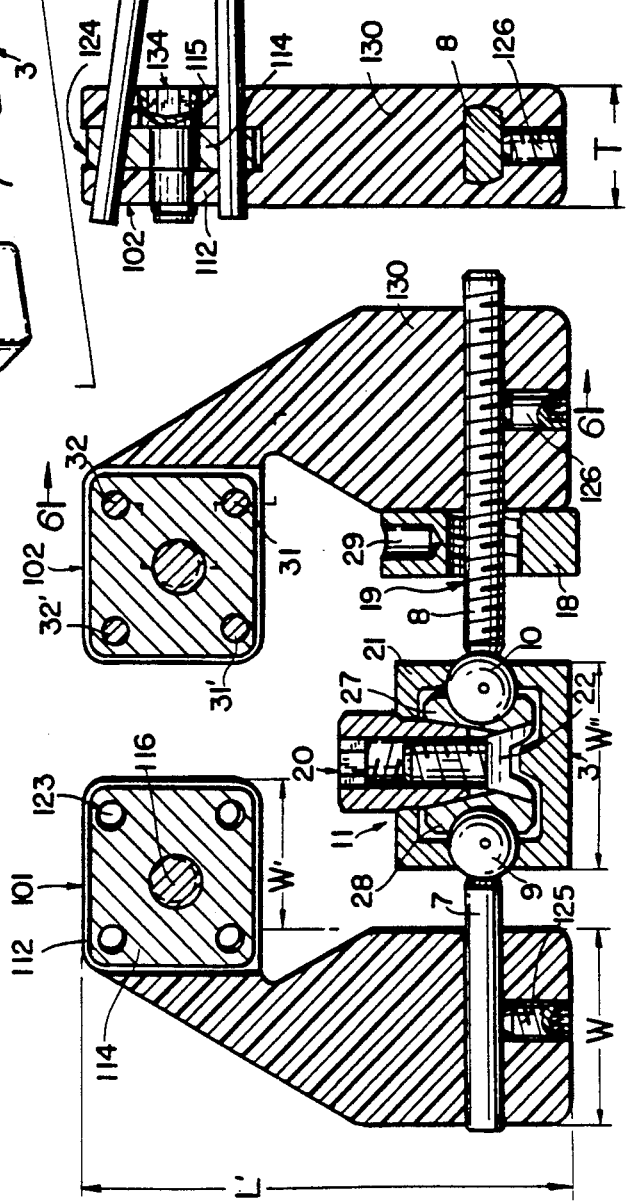

AUXILIARY DEVICE FOR OSTEOSYNTHESIS

RELATED CASE

This application is a continuation-in-part of copending application, Ser. No. 08/058,502, filed May 5, 1993 now abandoned.

BACKGROUND OF THE INVENTION

The invention relates to an orthopedic appliance, often referred to as an external fixator, for stabilized maintenance of spaced portions of a bone fracture and for the selective and progressive incremental adjustment thereof in the course of osteosynthesis, i.e., bone healing at the fracture. The invention has particular use in application to small bone fractures, as of the hand or foot.

From German Patent DE-3,701,533 C2 (and its corresponding U.S. Pat. No. 4,988,349), a fixator of the character indicated is known wherein a short central spacer has flexible connection at its respective ends, via twin ball joints, to separate arms which can be so selectively clamped as to provide a wide range of universal angular setting between the two arms, thereby providing a wide range of adjustment for bone-fastener units that anchor bone screws or pins via selectively adjustable fixation of such units to the respective arms. The design permits swivel and height adjustment of the bone-fastener units via individually locked ball joints at the central spacer, thereby creating added freedom of adjustment over a widened overall angular range. Thus, even very complex bone positions and their fine adjustment can be controlled by the surgeon.

When applying an external fixator in the area of the hand and of individual fingers, the surgeon also needs a maximum range of adjustment of single elements in relation to each other. At the same time, however, the structural elements should be kept small enough so that they will interfere to a minimum degree with movements of the hand, for example. The fixator of said patent has serious limitations in such a small-bone context.

BRIEF STATEMENT OF THE INVENTION

It is the object of the invention to provide an improved auxiliary device for osteosynthesis, namely, an external-fixator construction (i) wherein overall dimensions may be kept to a minimum, (ii) wherein basic design can be simple without impairing reliable releasably locked performance of the various structural elements, (iii) wherein a wide range of angle adjustability can be available with simplified locking, (iv) wherein multiple bone screws or pins can also be readily and adjustably clamped to the respective ends of the fixator with simplified locking, and (v) wherein substantially improved applicability can be achieved for small-bone fixation.

The invention achieves this object with a reduced-scale and simplified construction (a) wherein each of two bone-screw clamping units utilizes a single clamp which can in one operation effectively establish fixed retention of a plurality of bone screws or pins, (b) wherein the respective clamping units are adjustably lockable in desired position along ball-jointed end arms (carrier rods), and (c) wherein a single operation is effective to clamp two centrally spaced ball joints, within a wide range of universally flexible articulated connections.

More specifically, each of the bone-screw clamping units comprises plural (i.e., at least two) flat plates in face-to-face adjacency, with plural spaced sets of aligned bores that are sized to receive an inserted bone screw or pin. These plates may be of rectangular, square or oval configuration, and they are characterized by spaced sets of transversely aligned bores, each set being adapted for insertional assembly to the shank of a bone screw or pin. Each clamping unit must comprise at least two such plates in face-to-face adjacency, and the selective actuation into and out of securely and accurately locked engagement to one or more bone screws or pins is determined by rotation of an eccentric bolt, thus shifting one with respect to the other of the plates. Preferably, each clamping unit consists of a plate-like body which is locally slit to divide its thickness dimension into two spaced plates, accommodating a shiftable central plate therebetween. The aligned bores of each set extend transversely through the body plates and the shiftable plate, and the eccentric bolt is journalled in the body plates, with its eccentric surface effectively journalled in the central, shiftable plate. One or more first sets of aligned holes are normal to the plates; other sets are preferably canted from the normal, and are convergently aligned for externally projected geometric intersection with a corresponding projection of one or more of the first sets, thus for example ensuring that convergent operative ends of bone pins can be brought into very close relation to each other at bone engagement.

Each of the clamping units is freely positionable along and is releasably securable to its carrier rod, and the inner end of each carrier rod terminates in a ball, which is the means of universal ball-joint connection to a central coupling or frame member. A single adjustment at this central frame member provides simultaneous releasably locking action of the frame member to the ball of each of the carrier rods, the locking action being fully contained within the frame member. The frame member and the clamping wedge structure by which both ball joints can be releasably locked require a minimum of structural thickness and bulk, thereby enabling the overall fixator to present minimum inconvenience or handicap to a small-bone region such as the hand.

For stretching or compressive action on bone in the course of healing while held by the fixator, one or both of the carrier rods has external threads, and a nut engaged to such threads may be incrementally rotated in small steps and in abutment with the body of one of the clamping units. This nut may be peripherally graduated with angle-marking indicia to enable the surgeon to note how much he has incrementally compressed or stretched the fixation span, from time-to-time in the course of bone healing.

DETAILED DESCRIPTION

The invention will be described for illustrative embodiments, in conjunction with the accompanying drawings, in which:

FIG. 1 is a partially exploded view in perspective of an external fixator of the invention;

FIG. 2 is an enlarged view in longitudinal section through longitudinally connected components of the fixator of FIG. 1;

FIG. 3 is a sectional view taken at 3—3 of FIG. 2;

FIG. 4 is a view similar to FIG. 1, for a second embodiment of the invention;

FIG. 5 is a view similar to FIG. 2, for the embodiment of FIG. 4; and

FIG. 6 is a sectional view taken at 6—6 of FIG. 5.

In FIGS. 1 to 3 of the drawings, an auxiliary device or external fixator of the invention is seen to comprise two like clamping units 1 and 2, respectively adapted to carry bone fasteners 4, 5 which may be bone pins or bone screws engaged to the clamping unit 2.

Each of the clamping units 1 (2) is freely positionable along one of two carrier rods 7 (8), and each of the carrier rods features a ball 9 (10), by which adjacent but spaced ends of the carrier rods are connected and retained in assembled relation to a central box-like annular frame 11, thus establishing a twin ball-joint assembly 3. While unlocked, each of the two carrier rods 7, 8 can be swivelled in any desired direction, so that rods 7, 8 can be oriented as desired for adaptation to the curvature of the bones to be immobilized by the fixator.

Specifically, each of the opposed walls 21 of frame 11 is formed with a ball-seating surface which flares in the inward, direction, and wedge-loading plates 27, 28, are interposed between the respective balls 9, 10 and an adjustable wedge mechanism 20, 22. As shown, this mechanism comprises a wedge element 22 with opposed flats which converge inwardly and act on corresponding flats of the respective plates 27, 28, wherein such coaction is designed to occur primarily in the region defined by and below the geometrical line between the centers of balls 9, 10. The other part of the mechanism is in axially retained relation to the frame 11 and comprises an adjustment element or rotatable jacking element 20 having an external socket for Allen-head wrench access. Elements 20, 22 have threaded formations and coaction, enabling wedge element 22 to drive plates 27, 28 laterally for selective clamping action against balls 9, 10 of their carrier rods 7, 8. As shown, the inner end of wedge element 22 is reduced and externally threaded, engaging the threaded bore of the inner end of element 20. Also, as shown, the inwardly projecting end of element 20 is frusto-conical and convergent to termination at or just short of the geometrical line between ball centers and this frusto-conical formation engages in corresponding sloped area of upper regions of plates 27, 28, so that the conical engagements and the wedge-flat engagements each contribute to ball-joint locking, respectively above and below the geometrical line between ball centers.

Each of the carrier rods 7, 8 may be externally threaded but, as shown, only rod 8 is threaded, for operative engagement by the internal threads 19 of a nut 18. Also shown is a preference that carrier rods be milled with opposing flats, for smoothly keyed reception in a conforming guide-bore formation in the body of each of the clamping units 1, 2. In FIG. 3, the section shown for carrier rod 8 reveals the proportions of the milled flats, and the described threads will be understood to be limited to the diametrically opposed rounded ends of the rod section, between the milled flats. Not only do the milled flats and the conforming contours of the guide bore in the clamping-unit body account for smoothly adjustable positioning of the clamping unit 2 along its carrier rod 8, but the lower flat presents an optimum surface for engagement by a set screw 26, to lock the clamping unit in a desired location along its rod 8. Similarly, carrier rod 7 is engaged by set 25. In addition, the nut 18 is incrementally adjustable when abutted to clamping unit 2, as in FIG. 2, to effect an incrementally adjusted jacking shift of the clamping unit 2 in the longitudinally outward direction, thus incrementally stretching an afflicted bone in the course of healing a fracture. And it will be understood that if nut 18 is assembled to its carrier rod 8 so as to abut the outer end of the body of clamping unit 2, it is also possible to effect an incremental longitudinal compression of the involved fracture. As shown, nut 18 is circumferentially inscribed with angularly spaced indicia and/or local sockets 29, to facilitate angular indexing and entry of data for a succession of different stretching or compressional adjustments of the position of clamping unit 2, in the course of a given prescription for healing the involved bone fracture.

As shown, each of the clamping units 1, 2 comprises a generally prismatic body 30 having progressively reduced length, width and thickness dimensions L, W, T, respectively. The length dimension L is oriented for transverse offset of an upper bone-screw/bone-pin clamping region C, with respect to a lower carrier-rod guidance region, which extends through the full width dimension W of body 30. The offset clamping region is characterized by a slot 24 which is central of the thickness dimension T, thereby defining two flat plate formations 12, 15 which are integral features of body 30. As shown, the depth of slot 24 substantially matches the width dimension W, so that the confronting flat inner surfaces of plate formations 12, 15 are substantially square, and a separate plate 14 of slightly reduced area is slidably fitted in slot 24, for face-to-face engagement with plate formations 12, 15. First spaced sets of aligned bores 23 are drilled in the composite of elements 12, 14, 15 on alignments normal to the flat plate surfaces, the same being adapted to receive and correspondingly locate one or more inserted bone-pin/bone-screw shanks, as at 31, 31'; and second spaced sets of aligned bores are drilled in the composite of elements 12, 14, 15 on alignments that are canted from normal to the flat plate surfaces, the same being adapted to receive and correspondingly locate one or more inserted bone-pin/bone-screw shanks 32, 32'. The spacings between sets of aligned bores are substantially equal, with each set fully contained by the composite of elements 12, 14, 15; and the centers of the respective elements 12, 14, 15 are bored for development of an eccentrically driven shifting displacement of the central plate 14 via a rotary pin or bolt 34 that is journalled in plate formations 12, 14. Specifically, pin 34 has an enlarged head (with an Allen-head socket) journalled in plate formation 15, a central eccentric 16 of lesser diameter journalled in the shiftable plate 14, and a further-reduced other end journalled in plate formation 12, with snap-ring retention against the outer surface of plate formation 12. The throw of eccentric action is more than enough to releasably yet securely bind one or more inserted bone-pin/bone-screw shanks to each of the clamping units 1, 2, merely upon a single Allen-wrench actuation of the involved rotatable bolt or pin 34.

A preference is indicated, by dashed lines 31", 32" in FIG. 1, that the canting of at least one of the aligned sets of bores in the composite 12, 14, 15 shall be such as to converge with the normal orientation of at least another one of the aligned sets of bores as to involve bore axis projection for geometric intersection at a point 35 that is offset from the clamping-unit body 30. With this arrangement, it is clear that bone pins at 31', 32' can be set as closely together as desired at bone engagement, merely by selecting the extent to which their shanks are inserted through aligned bores in the composite 12, 14, 15, prior to eccentrically driven clamping of pins 31', 32' by a single wrenched partial turn of pin 34.

It is also clear that by having the ball joints fully contained by the box-like frame 11, the clamping units 1, 2 have a great range of adjustable positioning on their respective carrier rods, up to a point of virtual adjacency to the ball ends by which they are connected to the double-ball joint assembly within frame 11. Still further, it will be noted that all external features of the described fixator assembly are realizable (i) with minimum mass of component parts, (ii) within the same minimum thickness T as described for each of the clamping units 1, 2, and (iii) with a single actuator to perform multiple releasable clamp settings at units 1, 2 and 3 of the assembly.

Compact assembly of the central double-ball joint unit 3 within frame 11 is achievable via fixed retention of the reduced end of a carrier rod in a local radially inward bore or socket of its ball, the same being transversely pinned into permanent assembly after each ball is in place within frame 11. Preferably, the reduced carrier-rod end is threaded, and the local radially inward bore of the ball is tapped for threaded carrier-rod engagement.

In the drawings, the capacity is shown for each of the clamping units 1, 2 to accommodate four pins 5, wherein the lower pair of spaced parallel bores will accommodate pins that are parallel to each other and normal to the clamp plates 12, 14, 15, and wherein the upper pair of spaced parallel bores will accommodate pins that are parallel to each other but inclined from the normal, for geometric axis intersection, as at 35 in FIG. 1. As a practical matter, however, the four sets of aligned bores in the plates 12, 14, 15 of each clamp are not needed at any given time, in that two bone-screw pins 5 or the like are generally all that are needed for a given use of the structure. Thus, the surgeon has choices: to use his two pins via the lower pair of parallel sets of bores that are normal to plates 12, 14, 15; or to use his two pins via the upper pair of parallel sets of bores that are inclined from the normal to plates 12, 14, 15; or to use his two pins via one of the lower and one of the upper sets of aligned bores, thus releasably clamping his two pins for a predetermined angular relation of the two pins. In all cases, a single rotary actuation of the eccentric drive 34 will establish a positive locking jam of plate 14 against both of the two pins, regardless of the aligned bores in which they have been inserted.

In the embodiment of FIGS. 4 to 6, the same double ball-joint assembly 3 described for FIGS. 1 to 3 serves two clamping units 101, 102* each of which is embodied in a clamping-unit body 130 of generally L-shape, whereby to enable plural pins 4, 5 clamped by units 101, 102 to be set at very close proximity, as when external fixation is needed for small-bone fracture repair. The generally L-shape of each body 130 is seen to have a base end of width W and thickness T for selectively clamped longitudinal mounting on one of the carrier rods 7 (8), but the length dimension L' of each body 130 exceeds the dimension L of FIGS. 1 to 3, in order that each clamping unit 101, 102 may safely clear interference with the ball-joint assembly 3, for a wide range of angular settings of the carrier rods 7 (8). The generally L-shape of each body 130 enables each clamping unit 101, 102 to be at axial offset W' from its base end; preferably, the axial offset W' exceeds one half the axial width W" of the ball-joint frame 11, thereby enabling such freedom of carrier-rod angular adjustment as to permit clamping units 101, 102 to abut, even for a clamped angularly canted orientation of the respective bodies 130. In all cases, pin positioning in the clamping units 101, 102 is as described for units 1, 2 of FIGS. 1 to 3.

* In FIGS. 4 to 6, parts of the clamping units 101, 102 corresponding to parts of the clamping units 1, 2 of FIGS. 1 to 3 have been given the same numbers, in the 100 series, adopted for the clamping-unit designations 101, 102.

What is claimed is:

1. An auxiliary osteosynthesis device for fastening spaced portions of a fractured bone via two clamping units (1, 2) each of which is adapted for mounted reception of at least two spaced bone-anchoring pins or screws (4, 5), the said clamping units being adjustably spaced and interconnected by a twin ball-joint assembly (3) that can be releasably locked in desired position and by an elongate carrier rod (7, 8) that is associated with each of the respective ball joints, each of said clamping units (1, 2) comprising at least two plates having flat surfaces in face-to-face adjacency and each of said plates having a set of bores transverse to the adjacent plate surfaces, the set of bores of one plate being in alignment with respect to the set of bores of an adjacent plate for the mounted reception of said at least two spaced bone-anchoring pins or screws and selectively operable means reacting between said adjacent plates for incrementally displacing said one plate with respect to said adjacent plate for developing misalignment of the bores of each set and thereby developing a clamped engagement of said adjacent plates to said at least two spaced bone-anchoring pins or screws.

2. An auxiliary device according to claim 1, in which said selectively operable means is a selectively rotatable means.

3. An auxiliary device according to claim 2, in which each of said sets of bores is on spaced alignment axes that are convergent.

4. An auxiliary device according to claim 2, in which each of said sets of bores is on spaced alignment axes that are parallel.

5. An auxiliary device according to claim 2, in which the number of plates is three, in face-to-face adjacency, thereby establishing a central plate sandwiched between two outer plates, said outer plates being integral formations of a clamping-unit body having a further bore for adjustably shiftable guidance along one of said carrier rods, and adjustable locking means carried by said body for releasably locking said body in a selected position along one of said carrier rods.

6. An auxiliary device according to claim 2, in which at least one of said carrier rods is externally threaded, and a nut engaged to said rod threading for selectively adjusted position-limiting abutment with one of said clamping units.

7. An auxiliary device according to claim 2, in which said twin ball-joint assembly is a self-contained retainer of the spaced balls of two ball joints, with provision of a single means for releasably locking both ball joints.

8. An auxiliary device according to claim 2, in which said ball-joint assembly comprises a rigid generally rectangular frame with mutually facing spaced concave ball-seating formations on a single axis of aligned bores through opposing sides of the generally rectangular frame, and means including an adjustably positionable wedge between said balls seated in the respective ball-seating formations for selectively and releasably driving said balls into clamped engagement with their respective seating formations.

9. An auxiliary device according to claim 2, in which said selectively rotatable means includes an eccentric reacting between said adjacent plates.

10. An external fixator for secure retention of separate portions of a fractured bone, said fixator comprising a twin ball-joint assembly wherein separate carrier rods extend in opposite directions from their respective connections to said assembly via the respective balls of said joints and wherein both said ball joints are releasably lockable to maintain a given orientation of said carrier rods with respect to each other, two bone-fastener modules each of which comprises a module body that is adjustably positionable along a different one of said carrier rods and releasably clampable in selected rod position; said twin ball-joint assembly comprising an annular body having peripherally continuous inner and outer surfaces, said annular body having aligned bores on a single alignment through opposite peripheral body locations, the inner surface of said annular body at each of said bores being characterized by an inwardly flared concave ball-seating formation adapted for seating support of the ball of each of the respective ball joints, the respective balls being received in each of said seating formations with a ball-connected carrier rod projecting externally of said annular body via the associated ball-seating bore, and a single selectively operable means including an adjustably positionable wedge between balls seated in the respective concave seating formations for selectively and releasably outwardly driving said balls into clamped engagement with their respective seating formations.

11. The external fixator of claim 10 wherein a separate wedge-loading plate is interposed between said wedge and each of the respective balls.

12. The external fixator of claim 11, wherein each wedge-loading plate has a concave spherical surface engaged to the ball to which it is adjacent.

13. The external fixator of claim 11, in which one of said separate wedge-loading plates has a concave ball-seating formation on one side and is interposed between said wedge and the ball adjacent to said one wedge-loading plate and between said frusto-conical formation and said adjacent ball, and the other of said separate wedge-loading plates is identical to said one wedge-loading plate and is interposed between said wedge and the other ball and between said frusto-conical formation and said other ball.

14. The external fixator of claim 10, wherein said selectively operable means includes a rotatable jacking element in axially retained relation to said annular body and having threaded engagement to said wedge on an axial alignment which is normal to the alignment of said bores.

15. The external fixator of claim 14, wherein said rotatable jacking element is journalled in said annular body and said jacking element has a frusto-conical formation having convergence opposed to the direction of wedge convergence, said threaded engagement being such that, for jacking-element rotation in one direction, said wedge and frusto-conical formation are drawn in the direction of relative approach and that, for jacking-element rotation in the opposite direction, said wedge and frusto-conical formation are relatively displaced away from each other, both said conical formation and said wedge being conjointly operative to drive both said ball-joint balls into locked seat engagement for jacking-element rotation in said one direction.

16. The external fixator of claim 15, in which the threaded engagement consists of an externally threaded end of said wedge engaged to a threaded bore of said rotatable jacking element.

17. The external fixator of claim 10, in which said module body has length, width and thickness dimensions wherein the length dimension encompasses a base end for selectively clamped carrier-rod engagement and a fastener-module end for selectively clamped mounting of one or more bone-anchoring pins or screws, and said base end having an elongate bore extending in the direction of the width dimension and sized for guided carrier-rod engagement.

18. The external fixator of claim 17, in which said fastener-module end is grooved to define two spaced flat plates that are integral formations of said module body, and a flat central plate interposed between and in face-to-face adjacency with said two spaced plates, all said plates having an aligned set of bores transverse to the adjacent plate surfaces, and selectively operable means reacting between said central plate and said two spaced plates for incrementally displacing said central plate with respect to said two spaced plates for developing a clamped engagement of said plates to an inserted bone-anchoring pin or screw.

19. The external fixator of claim 17, in which said module body is of substantially uniform thickness.

20. The external fixator of claim 17, in which said module body is generally rectangularly prismatic.

21. The external fixator of claim 17, in which said module body is generally L-shaped, said base end being the free end of one of the arms of the L-shape and said fastener-module end being the free end of the other arm of the L-shape, whereby the fastener-module end is at radial and axial offset from base-end accommodation of carrier-rod engagement.

22. The external fixator of claim 21, in which the extent of axial offset exceeds one-half the effective width-dimension of said twin ball-joint assembly.

23. An auxiliary osteosynthesis device for fastening spaced portions of a fractured bone via two clamping units (1, 2) each of which is adapted for mounted reception of at least two spaced bone-anchoring pins or screws (4, 5), the said clamping units being adjustably spaced and interconnected by a twin ball-joint assembly (3) that can be releasably locked in desired position and by an elongate carrier rod (7, 8) that is associated with each of the respective ball joints, each of said clamping units (1, 2) comprising at least two plates having flat surfaces in face-to-face adjacency and said plates having, for the mounted reception of each bone-anchoring pin or screw, an aligned set of bores (23) transverse to the adjacent plate surfaces, and a single selectively operable means reacting between adjacent plates for incrementally displacing one plate with respect to an adjacent plate for developing misalignment of the bores of each set and thereby developing a clamped engagement of said plates to at least two spaced bone-anchoring pins or screws.

* * * * *